(12) United States Patent
Louw

(10) Patent No.: US 11,357,732 B2
(45) Date of Patent: *Jun. 14, 2022

(54) CAPSULE WITH VOLUME-ADJUSTABLE INTERNAL DIAPHRAGM

(71) Applicant: ComboCap, Inc., New York, NY (US)

(72) Inventor: Tobias Johan Louw, New York, NY (US)

(73) Assignee: ComboCap, Inc., Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/766,976

(22) PCT Filed: Oct. 10, 2016

(86) PCT No.: PCT/US2016/056276
§ 371 (c)(1),
(2) Date: Apr. 9, 2018

(87) PCT Pub. No.: WO2017/062951
PCT Pub. Date: Apr. 13, 2017

(65) Prior Publication Data
US 2018/0289625 A1 Oct. 11, 2018

Related U.S. Application Data

(60) Provisional application No. 62/239,435, filed on Oct. 9, 2015, provisional application No. 62/239,454, filed
(Continued)

(51) Int. Cl.
| | | |
|---|---|---|
| *A61K 9/48* | (2006.01) | |
| *A61K 45/06* | (2006.01) | |
| *A61K 31/01* | (2006.01) | |
| *A61K 31/05* | (2006.01) | |
| *A61K 31/201* | (2006.01) | |
| *A61K 31/202* | (2006.01) | |
| *A61K 31/203* | (2006.01) | |
| *A61K 31/375* | (2006.01) | |
| *A61K 31/525* | (2006.01) | |
| *A61K 31/60* | (2006.01) | |
| *A61K 33/06* | (2006.01) | |
| *A61K 33/18* | (2006.01) | |
| *A61K 33/26* | (2006.01) | |
| *A61K 33/42* | (2006.01) | |
| *A61K 31/616* | (2006.01) | |
| *A61K 31/122* | (2006.01) | |
| *A61K 31/137* | (2006.01) | |
| *A61K 47/12* | (2006.01) | |

(Continued)

(52) U.S. Cl.
CPC ............ *A61K 9/4808* (2013.01); *A61K 9/485* (2013.01); *A61K 9/4858* (2013.01); *A61K 9/4875* (2013.01); *A61K 31/01* (2013.01); *A61K 31/05* (2013.01); *A61K 31/122* (2013.01); *A61K 31/137* (2013.01); *A61K 31/192* (2013.01); *A61K 31/201* (2013.01); *A61K 31/202* (2013.01); *A61K 31/203* (2013.01); *A61K 31/353* (2013.01); *A61K 31/355* (2013.01); *A61K 31/375* (2013.01); *A61K 31/4458* (2013.01); *A61K 31/525* (2013.01); *A61K 31/60* (2013.01); *A61K 31/616* (2013.01); *A61K 33/06* (2013.01); *A61K 33/18* (2013.01); *A61K 33/26* (2013.01); *A61K 33/42* (2013.01); *A61K 35/741* (2013.01); *A61K 36/53* (2013.01); *A61K 36/71* (2013.01); *A61K 45/06* (2013.01); *A61K 47/12* (2013.01); *A61K 2035/115* (2013.01)

(58) Field of Classification Search
None
See application file for complete search history.

(56) References Cited

U.S. PATENT DOCUMENTS 1,510,260 A * 9/1924 Cyrenius ................. A61J 3/071
206/508
3,066,501 A * 12/1962 Stafford ............... A44C 11/002
63/39
(Continued)

FOREIGN PATENT DOCUMENTS

| EP | 2777802 A1 | 9/2014 |
|---|---|---|
| JP | 2006050933 A * | 2/2006 |

(Continued)

OTHER PUBLICATIONS

Capsugel® capsule size reference 2 pages (Year: 2013).*
(Continued)

*Primary Examiner* — Robert A Wax
*Assistant Examiner* — Caralynne E Helm
(74) *Attorney, Agent, or Firm* — DLA Piper LLP

(57) ABSTRACT

A two-compartment capsule includes a body, a diaphragm between which seals off the body and provides a first compartment to hold a first ingredient, and a cap applied to the body whereby a space between the inner portion of the cap and the diaphragm defines a second compartment for holding a second ingredient. This disclosure also provides certain ranges for the volumes of the first compartment and the second compartment, as well as a volume ratio of the first compartment to the second compartment, lengths of the first and second compartments, and the length of contact between a sidewall of the diaphragm and a sidewall of the body. Furthermore, particular ingredients and formulations for the two-compartment capsule where volume is critical for a therapeutic effect are disclosed.

17 Claims, 9 Drawing Sheets

Related U.S. Application Data on Oct. 9, 2015, provisional application No. 62/239,442, filed on Oct. 9, 2015.

(51) Int. Cl.
| | |
|---|---|
| *A61K 31/192* | (2006.01) |
| *A61K 31/353* | (2006.01) |
| *A61K 31/355* | (2006.01) |
| *A61K 31/4458* | (2006.01) |
| *A61K 35/741* | (2015.01) |
| *A61K 36/53* | (2006.01) |
| *A61K 36/71* | (2006.01) |
| *A61K 35/00* | (2006.01) |

(56) References Cited

U.S. PATENT DOCUMENTS

| | | | | |
|---|---|---|---|---|
| 3,927,195 | A | * 12/1975 | Messora | A61J 3/071 |
| | | | | 424/454 |
| 4,339,428 | A | 7/1982 | Tencza | |
| 4,748,058 | A | * 5/1988 | Craig, Jr. | A47G 33/06 |
| | | | | 428/18 |
| 5,223,265 | A | 6/1993 | Wong | |
| 5,387,421 | A | 2/1995 | Amidon et al. | |
| 5,394,980 | A | 3/1995 | Tsai | |
| 7,670,612 | B2 | 3/2010 | Miller | |
| 2003/0199481 | A1 | * 10/2003 | Garavani | A61K 9/4866 |
| | | | | 514/165 |
| 2005/0123603 | A1 | 6/2005 | Dalland et al. | |
| 2006/0280794 | A1 | 12/2006 | Hamaguchi et al. | |
| 2007/0212411 | A1 | 9/2007 | Fawzy et al. | |
| 2007/0259034 | A1 | 11/2007 | Steele et al. | |
| 2008/0213320 | A1 | 9/2008 | Eisenstein et al. | |
| 2008/0287368 | A1 | 11/2008 | Yu et al. | |
| 2009/0087483 | A1 | 4/2009 | Sison | |
| 2010/0048704 | A1 | 2/2010 | Vermeer et al. | |
| 2010/0209389 | A1 | * 8/2010 | McInnes | A61K 9/4808 |
| | | | | 424/85.4 |
| 2012/0209336 | A1 | * 8/2012 | Jackson | A61B 17/7008 |
| | | | | 606/305 |
| 2012/0269868 | A1 | 10/2012 | Faerstein | |
| 2014/0212482 | A1 | 7/2014 | Miller | |
| 2014/0273150 | A1 | 9/2014 | Angel | |
| 2014/0302133 | A1 | 10/2014 | Van Rooyen et al. | |
| 2015/0246768 | A1 | 9/2015 | Talon | |
| 2016/0038425 | A1 | 2/2016 | Fang et al. | |
| 2018/0296489 | A1 | 10/2018 | Louw | |

FOREIGN PATENT DOCUMENTS

| | | |
|---|---|---|
| NL | 7610038 A | 3/1978 |
| WO | 2013050973 A1 | 4/2013 |
| WO | 2014202412 | 12/2014 |
| WO | 2017062951 | 4/2017 |
| WO | 2017062954 | 4/2017 |
| WO | 2017062956 | 4/2017 |

OTHER PUBLICATIONS

Physical Properties of Fats and Oils reference www.dgfett.de/material/physikalische_eigenschaften.pdf 29 pages (Year: 2005).*
Aspirin safety data sheet 7 pages (Year: 2015).*
Cadé Vcaps® Plus Capsules 12 pages (Year: 2012).*
Extended European Search Report for European Patent Application No. 16854535.8 dated Apr. 2, 2019.
Extended European Search Report for European Patent Application No. 16854536.6 dated Apr. 3, 2019.
Extended European Search Report for European Patent Application No. 16854537.4 dated Mar. 29, 2019.
International Search Report and Written Opinion for PCT/US2016/056276 dated Jan. 10, 2017.
International Search Report and Written Opinion for PCT/US2016/056285 dated Jan. 10, 2017.
International Search Report and Written Opinion for PCT/US2016/056293 dated Jan. 23, 2017.
Johnson www.merckmanuals.com/home/disorders-of-nutrition/vitamins/overview-of-vitamins# 9pages (year: 2020).

* cited by examiner

CAPSULE WITH VOLUME-ADJUSTABLE INTERNAL DIAPHRAGM

CROSS-REFERENCE TO RELATED APPLICATIONS

This application is a U.S. national stage filing under 35 U.S.C. § 370 of International Application No. PCT/US2016/056276, filed Oct. 10, 2016, entitled "Capsule with Volume-Adjustable Internal Diaphragm," which claims priority to and benefit of U.S. Provisional Application Ser. No. 62/239,435, filed Oct. 9, 2015, entitled "Capsule with Volume-Adjustable Internal Diaphragm," U.S. Provisional Application Ser. No. 62/239,454, filed Oct. 9, 2015, entitled "Capsule with Internal Diaphragm for Improved Bioavailability," and U.S. Provisional Application Ser. No. 62/239,442, filed Oct. 9, 2015, entitled "Capsule with Internal Diaphragm and Solid Ingredients," each of which is hereby incorporated herein by reference in its entirety.

SUMMARY

Embodiments described herein are directed to a multi-compartment capsule comprising a body; a diaphragm, having two sidewalls and a bottom, extending into the body and defining a first compartment between an outer surface of the diaphragm and an inner surface of the body; and a cap mounted to an outer surface of the body and opposed to the diaphragm, and defining a second compartment between an inner surface of the diaphragm and the cap; wherein the two sidewalls of the diaphragm extend along the inner surface of the body and are aligned with an open end of the body.

In some embodiments, the first compartment has a volume of about 423 $mm^3$ to about 743 $mm^3$. In some embodiments, the second compartment has a volume of about 176 $mm^3$ to about 497 $mm^3$.

In some embodiments, the volume ratio of the first compartment to the second compartment is about 0.84 to about 4.2. In some embodiments, the length of the second compartment is about 5 mm to about 11.75 mm. In some embodiments, the length of the second compartment is less than 7 mm. In some embodiments, the length of the second compartment is about 5 mm to about 7 mm. In some embodiments, the length of the second compartment is greater than 10 mm. In some embodiments, the length of the second compartment is about 10 mm to about 11.75 mm.

In some embodiments, the length of the first compartment is about 8 mm to about 25 mm.

In some embodiments, the volume of the first compartment is less than about 500 $mm^3$. In some embodiments, the volume of the second compartment is less than about 500 $mm^3$. In some embodiments, the volume of the first compartment is greater than about 500 $mm^3$. In some embodiments, the volume of the second compartment is greater than about 500 $mm^3$.

In some embodiments, the capsule is about 23.5 mm in length. In some embodiments, the capsule is a size 00 capsule. In some embodiments, the length of contact between a sidewall of the diaphragm and a sidewall of the body is about 0.91 mm to about 8.5 mm.

In some embodiments, the bottom of the diaphragm may be flattened. In some embodiments, the bottom of the diaphragm may be curved. In some embodiments, the bottom of the diaphragm may be substantially or partially flattened.

In some embodiments, the first compartment comprises an ingredient that is volume-critical. In some embodiments, the second compartment comprises an ingredient that is volume-critical. In some embodiments, the first compartment and second compartment each comprise an ingredient that is volume-critical.

In some embodiments, the first compartment and the second compartment each have sufficient volume to administer a therapeutically effective dose of an ingredient.

In some embodiments, the volume-critical ingredient comprises aspirin. In some embodiments, the volume-critical ingredient comprises from about 10 mg to about 500 mg of aspirin. In some embodiments, the volume-critical ingredient may comprise about 1 mg to about 100 mg of a statin. In some embodiments, the compartment comprising aspirin has a volume of about 50 $mm^3$ to about 1000 $mm^3$, and the other compartment has a volume of about 50 $mm^3$ to about 1000 $mm^3$.

In some embodiments, the volume-critical ingredient comprises a statin. The statin may be selected from the group consisting of atorvastatin, fluvastatin, lovastatin, pitavastatin, pravastatin, rosuvastatin, simvastatin, and combinations thereof. The statin may be in an amount of about 1 mg to about 100 mg. In some embodiments, the other compartment may comprise a second ingredient, such as, for example, aspirin, triiodothyronine, a statin, a probiotic, a digestive enzyme, or combinations thereof. In some embodiments, the compartment comprising a statin has a volume of about 50 $mm^3$ to about 1000 $mm^3$, and the other compartment has a volume of about 50 $mm^3$ to about 1000 $mm^3$.

In some embodiments, the volume-critical ingredient comprises a pharmaceutical agent. In some embodiments, the pharmaceutical agent is selected from the group consisting of aspirin, a statin, ipriflavone, cohosh, castus, coenzyme Q10 (CoQ10), gauifenesin, althea root, antimony pentasulfide, creosote, guaiacolsulfonate, ipecacuanha (syrup of ipecac), levoverbenone, potassium iodide, senega, tyloxapol, ammonium chloride, salbutamol, albuterol, levosalbutamol, levalbuterol, pirbuterol, epinephrine, ephedrine, terbutaline, salmeterol, clenbuterol, formoterol, bambuerol, indacaterol, ephrinesulfate, ticlopidine, clopidogrel, prasugrel, ticagrelor, cilostazol, vorapaxar, trifusal, dipyridamole, a tocotrienol, and combinations thereof.

In some embodiments, the first compartment comprises aspirin in an amount of about 10 mg to about 500 mg and the second compartment comprises an oil in an amount of about 10 mg to about 1000 mg. In some embodiments, the first compartment comprises a tocotrienol and the second compartment comprises vitamin B6, vitamin B12, or a combination thereof. In some embodiments, the first compartment comprises an oil which is volume-critical and the second compartment comprises a second ingredient which is volume-critical.

In some embodiments, the second ingredient is selected from an oil, a powder, a liquid, a microbead, a beadlet, a granule, a semi-solid, a gel, or a combination thereof.

DETAILED DESCRIPTION

Figure 1:
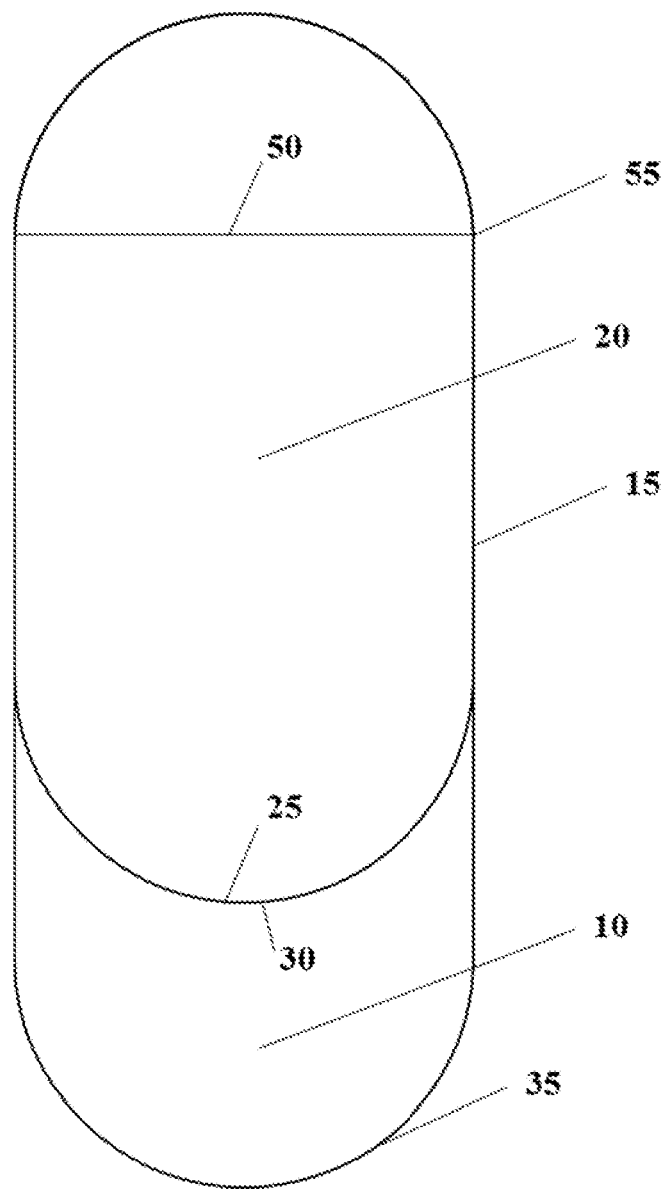
FIG. 1 illustrates a cross-sectional view of a capsule of embodiments herein wherein the first (lower) compartment has a volume of about 423 $mm^3$ and the second (upper) compartment has a volume of about 497 $mm^3$.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention, which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entireties. Nothing herein is to be construed as an admission that the invention is not entitled to antedate such disclosure by virtue of prior invention.

It must also be noted that as used herein and in the appended claims, the singular forms "a," "an," and "the" include plural references unless the context clearly dictates otherwise. Thus, for example, reference to "an ingredient" is a reference to one or more ingredients and equivalents thereof known to those skilled in the art, and so forth.

As used herein, the term "about" means plus or minus 10% of the numerical value of the number with which it is being used. Therefore, about 50 mm means in the range of 45 mm-55 mm.

The term "patient" or "subject" as used herein is an animal, particularly a human, suffering from an unwanted disease or condition that may be treated by the therapeutic and/or other compositions described herein.

"Optional" or "optionally" means that the subsequently described event or circumstance may or may not occur, and that the description includes instances where the event occurs and instances where it does not.

Throughout the specification of the application, various terms are used such as "primary," "secondary," "first," "second," and the like. These terms are words of convenience used to distinguish between different elements, and such terms are not intended to limit how the different elements may be used.

As used herein, the term "medicament" or "therapeutic" means an agent used to treat, combat, ameliorate, prevent or improve an unwanted condition or disease of a subject.

A "therapeutically effective amount" or "effective amount" of a composition is an amount necessary or sufficient to achieve the desired result. The activity contemplated by the embodiments herein includes medically therapeutic, cosmetically therapeutic, and/or prophylactic treatment, as appropriate. A therapeutically effective amount of the compound of embodiments herein is typically an amount such that when it is administered in a physiologically tolerable excipient composition, it is sufficient to achieve an effective systemic concentration or local concentration in or on a tissue to achieve the desired therapeutic or clinical outcome.

The terms "treat," "treated," and "treating," as used herein, refer to therapeutic treatment, cosmetic treatment, and/or prophylactic or preventative measures, wherein the object is to prevent or slow down (lessen) an undesired physiological condition, disorder, or disease, or to obtain beneficial or desired clinical results. For the purposes of this invention, beneficial or desired clinical results include, but are not limited to, alleviation of symptoms; diminishment of the extent of the condition, disorder, or disease; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease. Treatment includes eliciting a clinically significant response without excessive levels of side effects.

As used herein, the term "consists of" or "consisting of" means that the formulation includes only the elements, steps, or ingredients specifically recited in the particular claimed embodiment or claim.

As used herein, the term "consisting essentially of" or "consists essentially of" means that the only active pharmaceutical ingredient in the formulation or method that treats the specified condition is the specifically recited therapeutic in the particular embodiment or claim.

Capsules are typically manufactured in certain standard sizes referred to as a capsule size designated by numerals, such as 000, 00, etc. Such capsules typically have two parts: a cap and a body, which are bonded or fitted together. One of the most common sizes is the 00 capsule. The typical 00 size capsule, in common with other capsules, has a standardized nominal volume. For instance, a 00 size capsule has a volume of approximately 0.95 milliliters. The typical nominal length of the cap (along the long axis of the capsule) is 11.8 mm±0.4 mm. The length of the body (also as a separate component) is 20.2 mm±0.4 mm. The overall assembled length of such a capsule is 23.5 mm±0.4 mm. The outside diameter of the cap is typically 8.5 mm±0.03 mm and the outside diameter of the body, which is slightly smaller than that of the cap, since typically the cap fits over the body when assembled, is 8.22 mm±0.03 mm. Other sizes of capsules each have their own nominal dimensions. In some embodiments herein, the capsule is a size 00 capsule. In some embodiments, the capsule size may be size 000, size 0, size 1, size 2, size 3, size 4, or size 5, or any size in between these sizes. In some embodiments, the capsule size may be elongated ("EL"), such that the size may be, for example, 00 EL. In some embodiments, the elongated capsule may add from about 50 mm$^3$ to about 150 mm$^3$ of additional volume to the first compartment, the second compartment, or a combination thereof. In some embodiments, the elongated capsule may add about 110 mm$^3$ of additional volume to the first compartment, the second compartment, or a combination thereof. In some embodiments, the elongation may be to any standard or non-standard length.

Embodiments herein are directed toward a two-compartment capsule comprising a cap, a diaphragm, and a body.

Some embodiments are directed to a multi-compartment capsule comprising a body; a diaphragm, having two sidewalls and a bottom, extending into the body and defining a first compartment between an outer surface of the diaphragm and an inner surface of the body; and a cap mounted to an outer surface of the body and opposed to the diaphragm, and defining a second compartment between an inner surface of the diaphragm and the cap; wherein the two sidewalls of the diaphragm extend along the inner surface of the body and are aligned with an open end of the body.

This disclosure is generally of a capsule of 00 size; this size is not at all limiting, but is merely illustrative. In some embodiments, the first compartment has a volume of about 422 mm$^3$ to about 743 mm$^3$. In some embodiments, for a size 00 capsule, the first compartment has a volume of about 420 mm$^3$, about 422 mm$^3$, about 425 mm$^3$, about 450 mm$^3$, about 475 mm$^3$, about 497 mm$^3$, about 500 mm$^3$, about 525 mm$^3$, about 550 mm$^3$, about 575 mm$^3$, about 600 mm$^3$, about 625 mm$^3$, about 650 mm$^3$, about 675 mm$^3$, about 700 mm$^3$, about 725 mm$^3$, about 743 mm$^3$, about 750 mm$^3$, or a range between any two of these values, including endpoints. In some embodiments, the volume of the first compartment is less than about 500 mm$^3$. In some embodiments, the volume of the first compartment is greater than about 500 mm$^3$.

In some embodiments, for a 00 sized capsule, the second compartment has a volume of about 176 mm$^3$ to about 497 mm$^3$. In some embodiments, the second compartment has a volume of about 175 mm$^3$, about 180 mm$^3$, about 185 mm$^3$, about 190 mm$^3$, about 200 mm$^3$, about 210 mm$^3$, about 225 mm$^3$, about 250 mm$^3$, about 275 mm$^3$, about 300 mm$^3$, about 325 mm$^3$, about 350 mm$^3$, about 375 mm$^3$, about 400 mm$^3$, about 425 mm$^3$, about 450 mm$^3$, about 475 mm$^3$, about 497 mm$^3$, about 500 mm$^3$, or a range between any two of these values, including endpoints. In some embodiments, the volume of the second compartment is less than about 500 mm$^3$. In some embodiments, the volume of the second compartment is greater than about 500 mm$^3$.

In some embodiments, the volume ratio of the first compartment to the second compartment is about 0.84 to about 4.2. In some embodiments, the volume ratio of the first compartment to the second compartment is about 0.84, about 1.0, about 1.5, about 2.0, about 2.5, about 3.0, about 3.5, about 4.0, about 4.2, or a range between any two of these values, including endpoints.

In some embodiments, the length of the second compartment is about 5 mm to about 11.75 mm. In some embodiments, the length of the second compartment is less than 7 mm. In some embodiments, the length of the second compartment is about 5 mm to about 7 mm. In some embodiments, the length of the second compartment is greater than 10 mm. In some embodiments, the length of the second compartment is about 10 mm to about 11.75 mm. In some embodiments, the length of the second compartment is about 5 mm, about 5.5 mm, about 6.0 mm, about 6.5 mm, about 7.0 mm, about 7.5 mm, about 8.0 mm, about 8.5 mm, about 9.0 mm, about 9.5 mm, about 10 mm, about 10.5 mm, about 11 mm, about 11.5 mm, about 11.75 mm, or a range between any two of these values, including endpoints.

In some embodiments, the length of the first compartment is about 8 mm to about 25 mm. In some embodiments, the length of the first compartment may be, for example, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, or any ranges between any two of these values, including endpoints. In some embodiments, the length of the first compartment is less than about 16 mm. In some embodiments, the length of the first compartment is about 5 mm to about 15 mm.

In some embodiments, the length of the second compartment is about 8 mm to about 24 mm. In some embodiments, the length of the second compartment may be, for example, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or any ranges between any two of these values, including endpoints.

Figure 2:
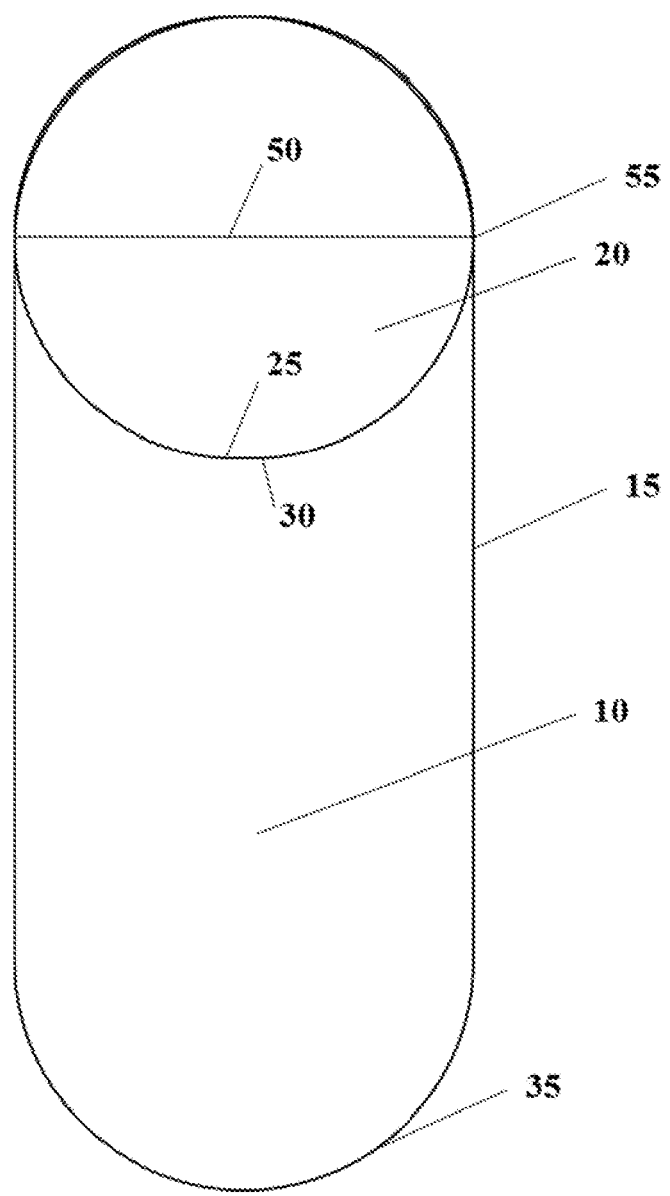
FIG. 2 illustrates a cross-sectional view of a capsule of embodiments herein wherein the first (lower) compartment has a volume of about 743 $mm^3$ and the second (upper) compartment has a volume of about 176 $mm^3$.
Figure 3:
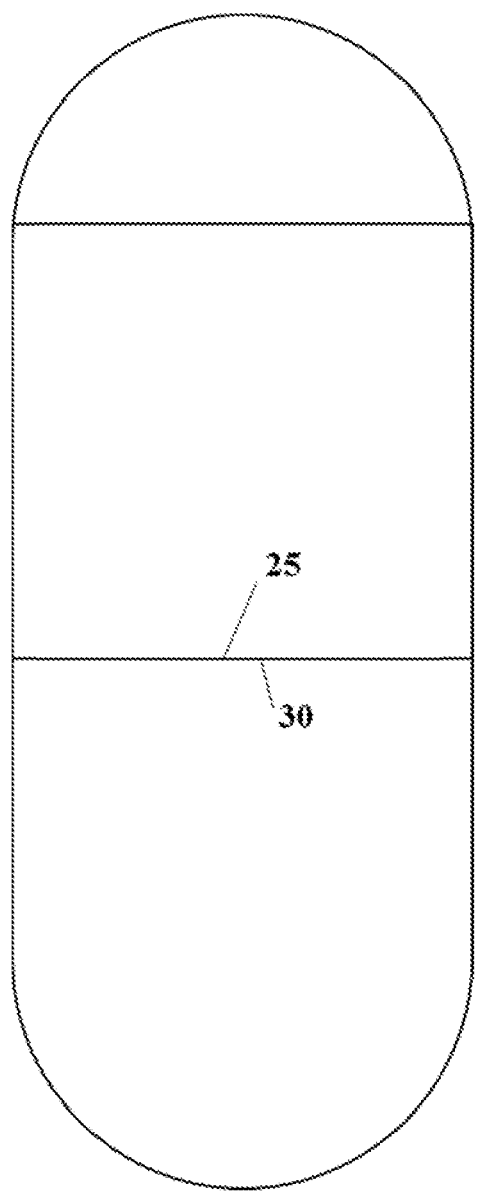
FIG. 3 illustrates a cross-sectional view of a capsule of embodiments herein with a flattened bottom.
Figure 4A:
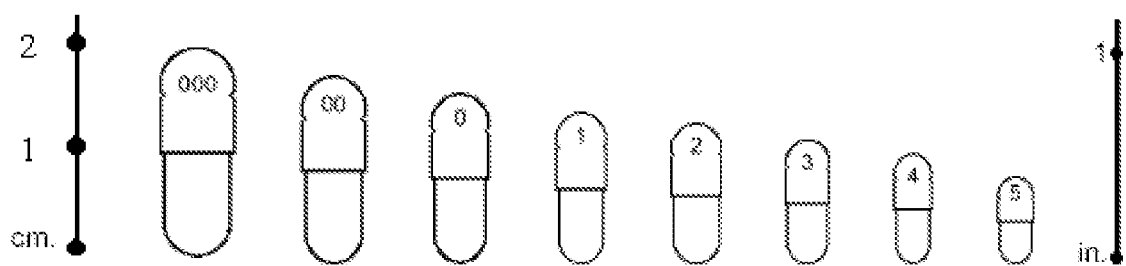
FIGS. 4A, 4B, and 4C illustrate standard and elongated TORPAC capsule sizes, which may be used in some embodiments described herein.
Figure 4B:
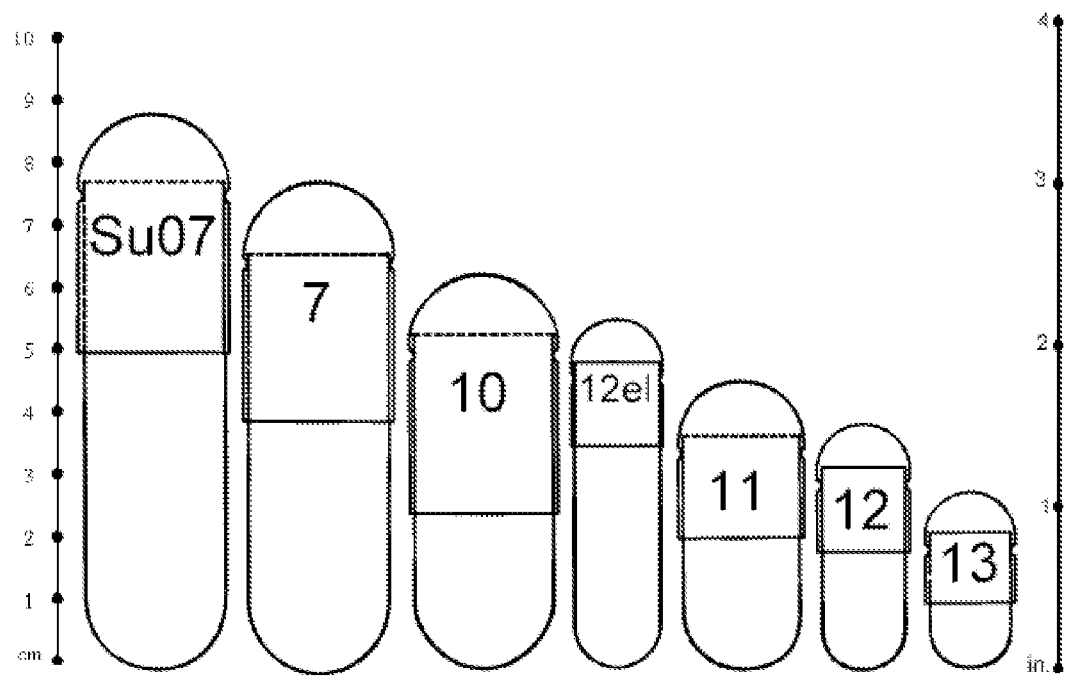
Figure 4C:
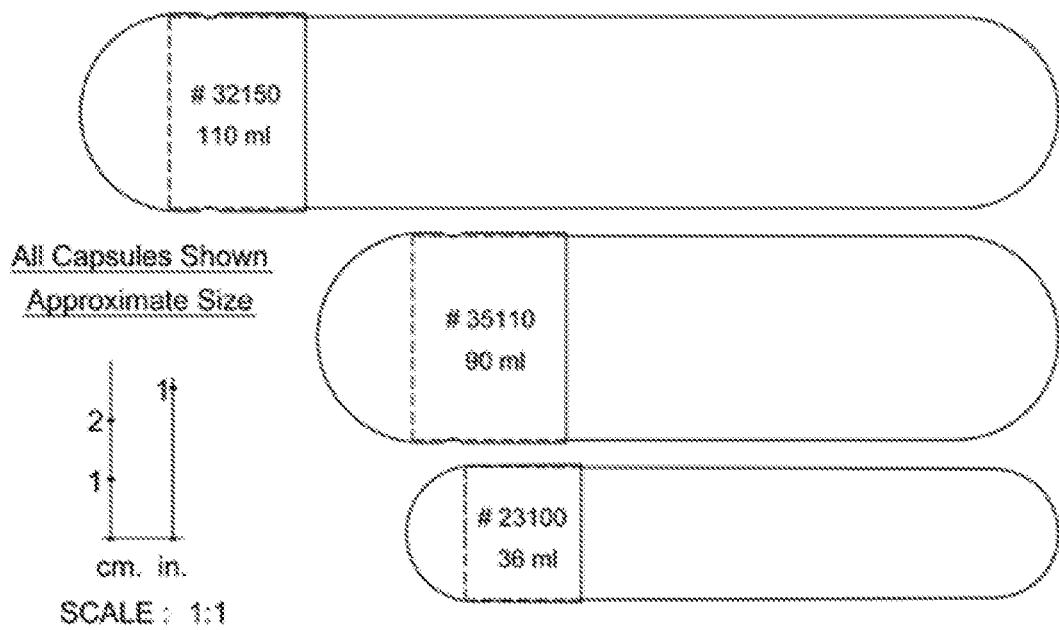
Figure 5:
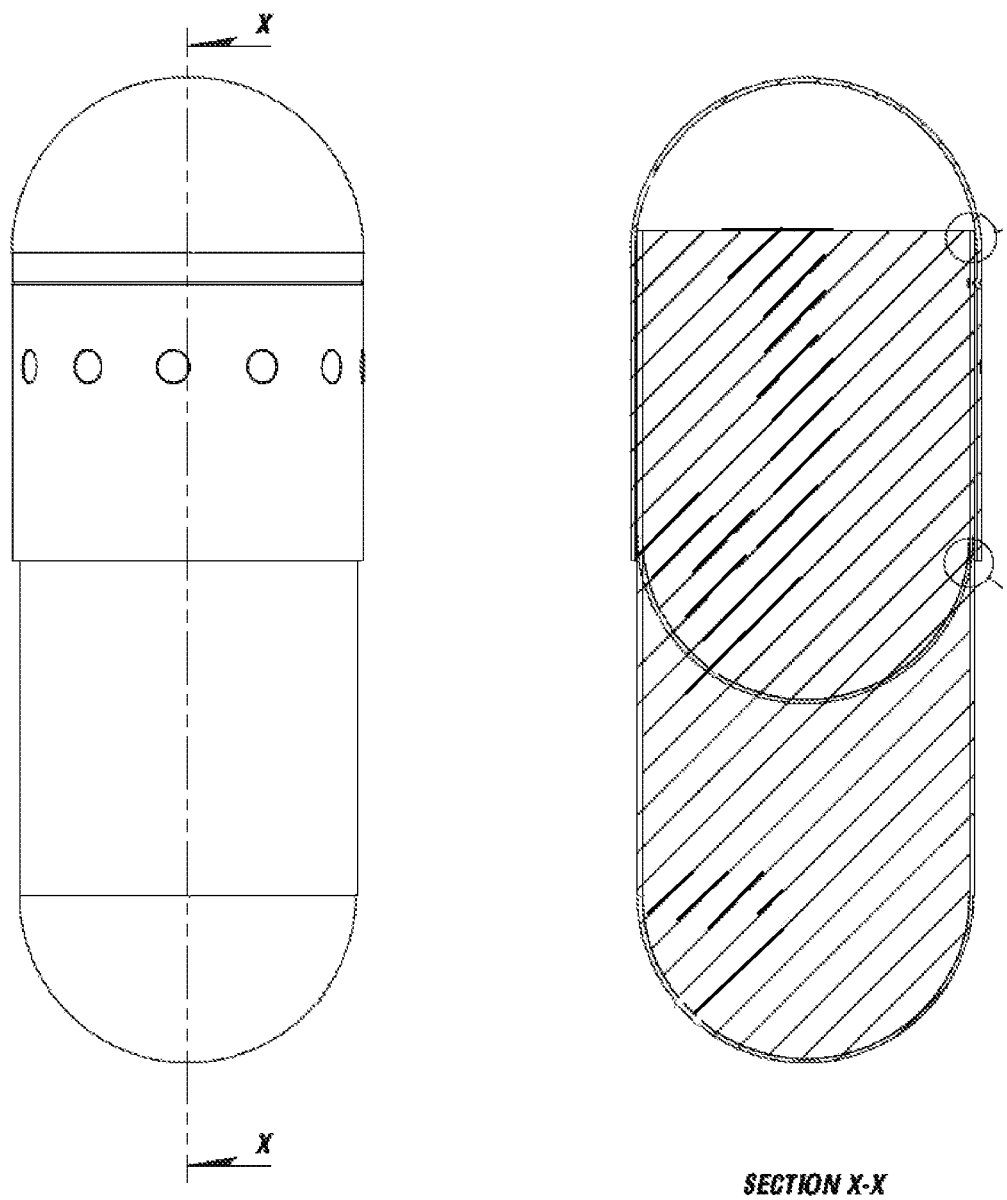
FIG. 5 illustrates a cross-sectional view of a capsule of embodiments herein wherein the first (lower) compartment has a volume of 421.51 mm$^3$ and the second (upper) compartment has a volume of 497.95 mm$^3$.
Figure 6:
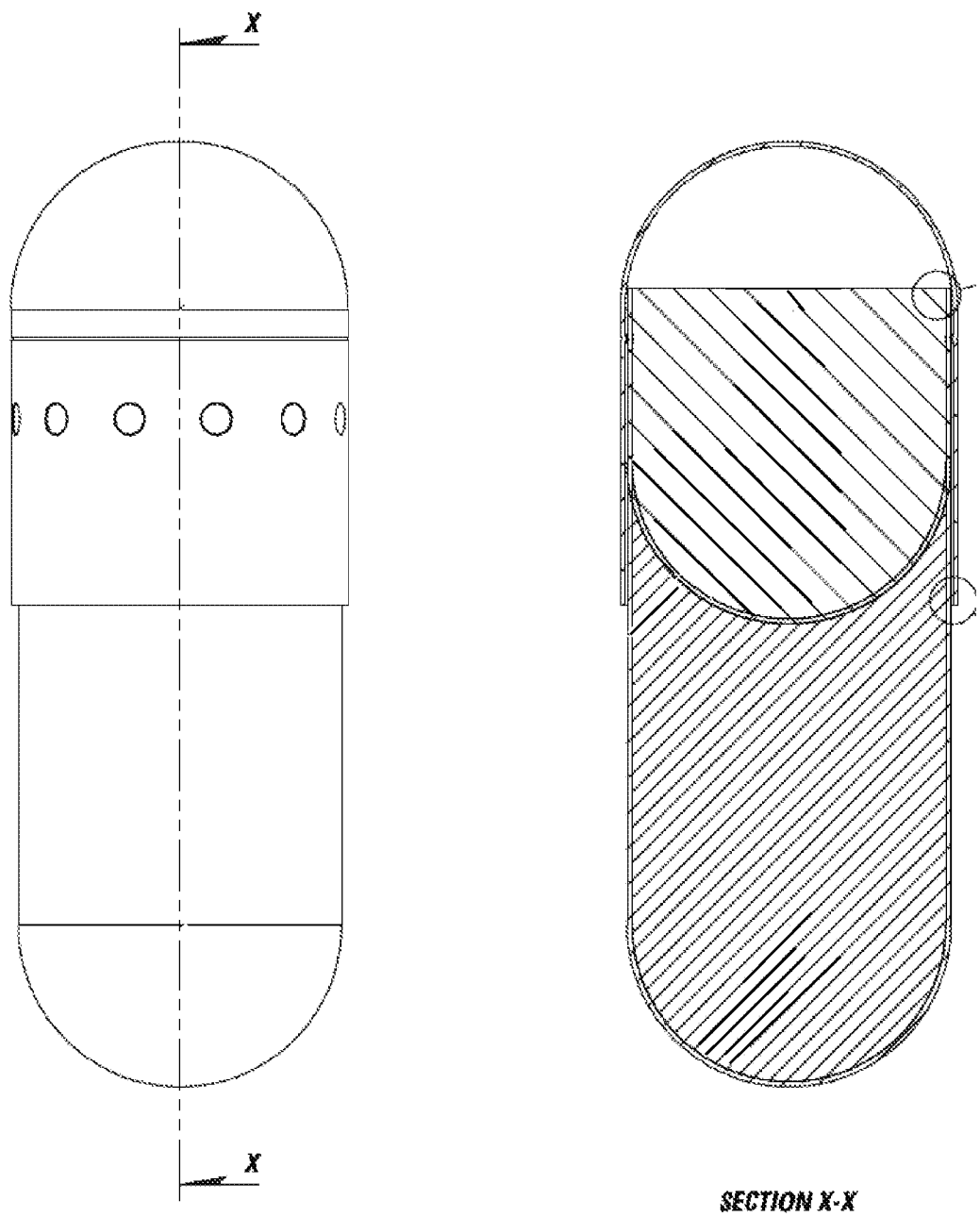
FIG. 6 illustrates a cross-sectional view of a capsule of embodiments herein wherein the first (lower) compartment has a volume of 570.05 mm$^3$ and the second (upper) compartment has a volume of 349.41 mm$^3$.
Figure 7:
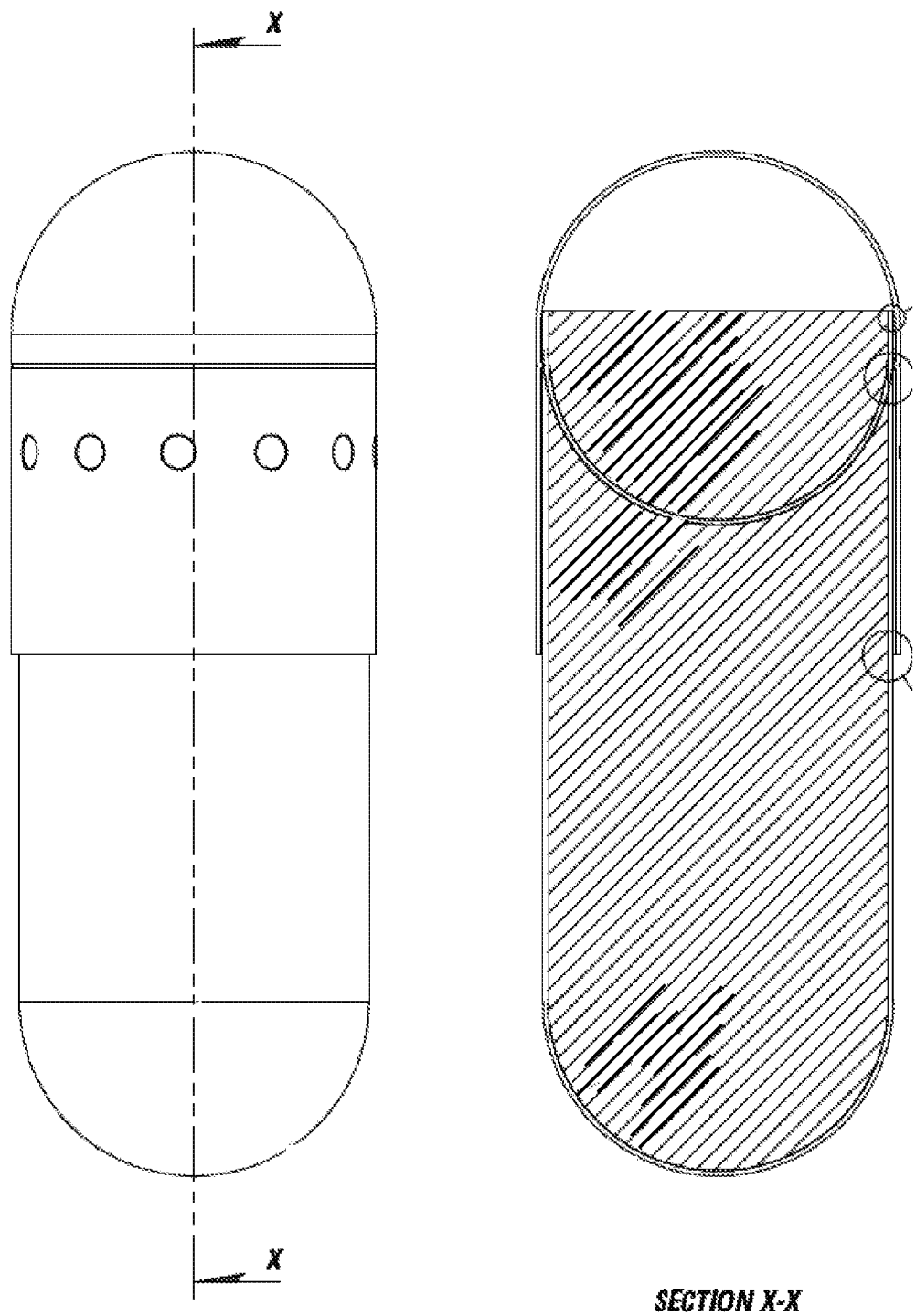
FIG. 7 illustrates a cross-sectional view of a capsule of embodiments herein wherein the first (lower) compartment has a volume of 743.35 mm$^3$ and the second (upper) compartment has a volume of 176.11 mm$^3$.

FIG. 1 shows in a cross-sectional view of a capsule of embodiments herein wherein the first compartment 10 has a volume of about 423 mm$^3$ and the second compartment 20 has a volume of about 497 mm$^3$. The body 15 is typically in the form of a digestible hard gelatin capsule for holding an ingredient 40 (e.g., an oil) in the first compartment 10. The nature of the ingredient held, of course, is not limiting and an oil is merely illustrative. The ingredients may be wet or dry (powder or liquid) and may, as usual, include excipients (inactive carriers) which are wet or dry. In some embodiments, fluids may be held in an air-tight and/or liquid-tight hermetically sealed chamber 45 defined by the body 15. The first compartment 10 may further include, in some embodiments, a low-pressure (sub-atmospheric) gas in its upper portion which will not react with the ingredient 40, such as nitrogen gas. Note that certain ingredients and/or excipients may be unstable and a non-reactive gas may be provided to preserve such unstable materials. The first compartment 10 may include, in some embodiments, a small bubble of air or any other gas which will not react with the ingredient 40. Separating the first compartment 10 from the second compartment 20 is a diaphragm 25, which, in some embodiments, may be made of a material similar to the body 15 (e.g., hard gelatin). The diaphragm 25 may be fabricated as a separate component from the body 15. In some embodiments, the body 15 is in the form of a hollow cylindrical tubular body defining its closed-end 35 and an opposed upper end defined by the lower wall 30 of the diaphragm 25. The upper end 50 of the diaphragm 25 may be open. In some embodiments, the upper end 50 of the diaphragm 25 is aligned with the upper end 55 of the body 15. In some embodiments, the lower wall 30 of the diaphragm 25 may be flattened, as shown in FIG. 3. FIG. 2 illustrates a cross-sectional view of a capsule of embodiments herein wherein the first compartment 10 has a volume of about 743 mm$^3$ and the second compartment 20 has a volume of about 176 mm$^3$. FIGS. 4A, 4B, 4C, 5, 6, and 7 illustrate additional aspects of a capsule of embodiments herein.

The components of the capsule described in embodiments herein are configured such that the pressure of the insertion need not be too great, thereby preventing a rupture of the capsule during assembly. In some embodiments, these capsules are sealed under a certain amount of pressure by the sealing machinery that bonds the body and diaphragm together as well as the cap and body. Thus, a goal here is that the sidewall contact area between the diaphragm and the body allows for optimum alignment of the diaphragm during insertion, resulting in an even edge at the top of the body/diaphragm mouth, providing a good seal both at the body perimeter and its sides. Also, it is intended that this sidewall contact provide adequate friction for the seal, in terms of the overall structure, integrity and robustness of the capsule. Thus, this configuration provides stability and adequate sidewall friction for the seal, which advantageously allows for high-volume manufacturing with small tolerances. The sealing process may include an application of pressure and heat to bond the gelatin of the capsule components (body, diaphragm and/or cap) where they overlap, not just a friction fit. In some embodiments, the sidewall friction is such that by itself it provides a level of orientation and stability in addition to that provided by the bonding of the components together. In some embodiments, if the diaphragm's diameter is reduced, it may be possible to insert a longer diaphragm into the capsule, thereby changing the available volumes in both the first and second compartments. In some embodiments, scaling the dimensions of the multi-compartment capsule described herein may result in a larger or smaller capsule with substantially the same ratios as described herein. In some embodiments, scaling the dimensions of the multi-compartment capsule described herein may result in a larger or smaller capsule with ratios different from those described herein.

Exemplary benefits of such two-compartment capsules may include increased patient compliance, a double-chamber controlled release, increased efficacy or bioavailability of ingredients due to co-administration, increased stability, and the ability to formulate difficult combinations of ingredients into one capsule, such as incompatible actives which can now be co-administered.

In some embodiments, the capsule is a size 00 capsule. In some embodiments, the capsule is about 23.5 mm in length. In some embodiments, the capsule is about 23.0, about 23.1 mm, about 23.5 mm, about 23.9 mm, about 24 mm in length or a range between any two of these values.

It has been found that if the length of this sidewall contact with the body is less than approximately 0.9 mm, the body-diaphragm seal is likely to fail. In some embodiments, a sidewall of the body and a sidewall of the diaphragm are in contact such that the rims of the body and the diaphragm are aligned with each other. In some embodiments, both the sidewall and rim of the diaphragm are sealed to the body. The sidewall may act both as a support and as a seal. In some embodiments, the length of contact between a sidewall of the diaphragm and a sidewall of the body is about 0.9 mm to about 8.5 mm. In some embodiments, the length of contact between a sidewall of the diaphragm and a sidewall of the body is about 0.9 mm, about 1.0 mm, about 1.25 mm, about 1.5 mm, about 2.00 mm, about 2.5 mm, about 3.0 mm, about 3.5 mm, about 4.0 mm, about 4.5 mm, about 5.0 mm, about 5.5 mm, about 6.0 mm, about 6.5 mm, about 7.0 mm, about 7.48 mm, about 7.5 mm, about 8.0 mm, about 8.5 mm, or a range between any two of these values, including endpoints.

In some embodiments, the bottom of the diaphragm may be curved. In some embodiments, the bottom of the diaphragm may be flattened. In some embodiments, the bottom of the diaphragm may be substantially or partially flattened. A flattened bottom may allow for an increased volume in the lower compartment.

In some embodiments, the first compartment comprises an ingredient that is volume-critical. In some embodiments, the second compartment comprises an ingredient that is volume-critical. In some embodiments, the first compartment and second compartment each comprise one or more ingredients that are volume-critical. As used herein, a volume-critical ingredient is an ingredient for which administration of a certain amount is required to be therapeutically effective (either on its own or with a second ingredient) or to make the second ingredient more bioavailable.

In some embodiments, the first compartment and the second compartment each have sufficient volume to administer a therapeutically effective dose of an ingredient.

In some embodiments, the volume-critical ingredient may include, for example, aspirin, a statin, triiodothyronine (T3), vitamin B6, vitamin B12, omega-3 oil, red palm oil, fish oil, krill oil, walnut oil, saw palmetto oil, castor oil, garlic oil, flaxseed oil, canola oil, soybean oil, cannabis oil, argan oil, coconut oil, peppermint oil, evening primrose oil, oregano oil, emu oil, cod liver oil, algae oil, grape seed oil, rose oil, clove oil, vitamin E oil, blueberry seed oil, raspberry seed oil, pumpkin seed oil, hemp oil, alpha linolenic acid, conjugated linoleic acid, docosahexaenoic acid, ginger oil, lavender oil, and combinations thereof. In some embodiments, the ingredient is selected from an oil, a powder, a liquid, a microbead, a beadlet, a granule, a semi-solid, a gel, or a combination thereof.

In some embodiments, the volume-critical ingredient may include, for example, alpha-carotene, beta-carotene, biotin, cadmium, caffeine, calcium, cinnamon, copper, curcumin, dexmethylphenidate, dicalcium phosphate, docosahexaenoic acid, folic acid, frankincense, glucosamine, gymnema, gymnema extract, iodine, iron, linoleic acid, lipoic acid, LOWAT, lutein, lycopene, magnesium, magnesium stearate, manganese, melatonin, molybdenum, niacin, oleic acid, palmitic, panthothenic acid, passion flower, phosphorus, a plant sterol, resvida, selenium, squalene, ginseng, tocopherols, vitamin A, vitamin B1, vitamin B2, vitamin B6, vitamin C, vitamin K, zinc, or a combination thereof.

In some embodiments, the volume-critical ingredient comprises aspirin. In some embodiments, the volume-critical ingredient comprises from about 10 mg to about 500 mg of aspirin. In some embodiments, the volume-critical ingredient comprises from about 81 mg to about 324 mg of aspirin. In some embodiments, one of the first or second compartment comprises aspirin in an amount of about 10 mg to about 500 mg. In some embodiments, the other compartment may comprise a statin in an amount of about 1 mg to about 100 mg. In some embodiments, the compartment comprising aspirin has a volume of about 50 $mm^3$ to about 1000 $mm^3$, and the other compartment has a volume of about 50 $mm^3$ to about 1000 $mm^3$.

In some embodiments, the volume-critical ingredient comprises a statin. The statin may be selected from the group consisting of atorvastatin, fluvastatin, lovastatin, pitavastatin, pravastatin, rosuvastatin, simvastatin, and combinations thereof. The statin may be in an amount of about 1 mg to about 100 mg. In some embodiments, the statin may be in an amount of about 5 mg to about 40 mg. In some embodiments, one of the first or second compartments comprises a statin in an amount of about 1 mg to about 100 mg. In some embodiments, the other compartment may comprise a second ingredient, such as, for example, aspirin, triiodothyronine, a statin, a probiotic, a digestive enzyme, or combinations thereof. In some embodiments, the compartment comprising a statin has a volume of about 50 $mm^3$ to about 1000 $mm^3$, and the other compartment has a volume of about 50 $mm^3$ to about 1000 $mm^3$.

In some embodiments, the volume-critical ingredient comprises a pharmaceutical agent. In some embodiments, the pharmaceutical agent is selected from the group consisting of aspirin, a statin, ipriflavone, cohosh, castus, coenzyme Q10 (CoQ10), gauifenesin, althea root, antimony pentasulfide, creosote, guaiacolsulfonate, ipecacuanha (syrup of ipecac), levoverbenone, potassium iodide, senega, tyloxapol, ammonium chloride, salbutamol, albuterol, levosalbutamol, levalbuterol, pirbuterol, epinephrine, ephedrine, terbutaline, salmeterol, clenbuterol, formoterol, bambuerol, indacaterol, ephrinesulfate, ticlopidine, clopidogrel, prasugrel, ticagrelor, cilostazol, vorapaxar, trifusal, dipyridamole, a tocotrienol, and combinations thereof.

In some embodiments, the first compartment comprises triiodothyronine (T3) and the second compartment comprises vitamin B6, vitamin B12, or a combination thereof. In some embodiments, the first compartment comprises a form or derivative of vitamin E, and the second compartment comprises vitamin B6, vitamin B12, or a combination thereof. In some embodiments, the form or derivative of vitamin E may be a tocotrienol, such as, for example, alpha tocotrienol, beta tocotrienol, gamma tocotrienol, delta tocotrienol, or any combination thereof.

In some embodiments, the first compartment comprises aspirin in an amount of about 10 mg to about 500 mg and the second compartment comprises an oil in an amount of about 10 mg to about 2000 mg.

In some embodiments, the first compartment comprises an oil which is volume-critical and the second compartment comprises a second ingredient which is volume-critical. In some embodiments, the capsule may include krill oil in the first compartment, and CoQ10 with or without a multivitamin in the second compartment. The krill oil may be in an amount of about 10 mg to about 2000 mg. The CoQ10 may be in an amount of about 10 mg to about 1000 mg. The multivitamin may be in an amount of about 1 mg to about 5000 mg.

In some embodiments, the capsule may include an omega-3 oil with or without red palm oil in the first compartment, and CoQ10 in the second compartment. The omega-3 oil may be in an amount of about 10 mg to about 2000 mg. The red palm oil may be in an amount of about 10 mg to about 2000 mg. The CoQ10 may be in an amount of about 10 mg to about 1000 mg.

In some embodiments, the triiodothyronine may be in the first compartment, and vitamin B6 and/or vitamin B12 may be in the second compartment. The triiodothyronine may be in an amount of about 5 mcg to about 500 mcg. The vitamin B6 may be in an amount of about 10 mg to about 1000 mg. The vitamin B12 may be in an amount of about 10 mcg to about 1000 mcg.

In some embodiments, the first compartment may comprise alpha-linolenic acid, and the second compartment may comprise chromium with or without CoQ10. The alpha-linolenic acid may be in an amount of about 10 mg to about 500 mg. The chromium may be in an amount of about 10 mcg to about 1000 mcg. The CoQ10 may be in an amount of about 10 mg to about 1000 mg.

In some embodiments, the first compartment may comprise krill oil and the second compartment may comprise vitamin K2. The krill oil may be in an amount of about 10 mg to about 2000 mg. The vitamin K2 may be in an amount of about 10 mcg to about 1000 mcg.

In some embodiments, the first compartment may comprise saw palmetto oil and the second compartment may comprise triiodothyronine. The saw palmetto oil may be in an amount of about 10 mg to about 1000 mg. The triiodothyronine may be in an amount of about 5 mcg to about 500 mcg.

In some embodiments, the first compartment may comprise an omega-3 oil, and the second compartment may comprise a statin with or without CoQ10. The omega-3 oil may be in an amount of about 10 mg to about 2000 mg. The statin may be in an amount of about 1 mg to about 100 mg. The CoQ10 may be in an amount of about 10 mg to about 1000 mg.

In another embodiment, the first compartment may comprise red palm oil, and the second compartment may comprise vitamin D, vitamin K2, a multivitamin, or a combination thereof. The red palm oil may be in an amount of about 10 mg to about 2000 mg. The vitamin D may be in an amount of about 10 IU to about 3000 IU. The vitamin K2 may be in an amount of about 10 mcg to about 1000 mcg. The multivitamin may be in an amount of about 1 mg to about 5000 mg.

In some embodiments, the first compartment may comprise red palm oil, and the second compartment may comprise lutein, lycopene, biotin, selenium, selenium (methionine), zinc, zinc (glyconate), or a combination thereof. The red palm oil may be in an amount of about 10 mg to about 2000 mg. The lutein may be in an amount of about 1 mg to about 30 mg. The lycopene may be in an amount of about 1 mg to about 30 mg. The biotin may be in an amount of about 0.01 mg to about 10 mg. The selenium or selenium (methionine) may be in an amount of about 1 mcg to about 200 mcg. The zinc or zinc (glyconate) may be in an amount of about 1 mg to about 45 mg.

In some embodiments, the first compartment may comprise an omega-3 oil and the second compartment may comprise frankincense, gymnema, gymnema extract, cinnamon, chromium, chromium (picolinate), vitamin B6, vitamin B12, or a combination thereof. The omega-3 oil may be in an amount of about 10 mg to about 2000 mg. The frankincense may be in an amount of about 1 mg to about 500 mg. The gymnema or gymnema extract may be in an amount of about 10 mg to about 1000 mg. The cinnamon may be in an amount of about 10 mg to about 1000 mg. The chromium or chromium (picolinate) may be in an amount of about 10 mg to about 1000 mg. The vitamin B6 may be in an amount of about 10 mg to about 1000 mg. The vitamin B12 may be in an amount of about 10 mcg to about 1000 mcg.

In some embodiments, the first compartment may comprise an omega-3 oil, and the second compartment may comprise resvida, lipoic acid, CoQ10, folic acid, vitamin B6, vitamin B12, or a combination thereof. The omega-3 oil may be in an amount of about 10 mg to about 2000 mg. The resvida may be in an amount of about 10 mg to about 1000 mg. The amount of lipoic acid may be in an amount of about 1 mg to about 1000 mg. The CoQ10 may be in an amount of about 10 mg to about 1000 mg. The folic acid may be in an amount of about 0.1 mcg to about 1000 mcg. The vitamin B6 may be in an amount of about 10 mg to about 1000 mg. The vitamin B12 may be in an amount of about 10 mcg to about 1000 mcg.

In some embodiments, the first compartment may comprise krill oil, red palm oil, or a combination thereof, and the second compartment may comprise oleic acid, linoleic acid, tocotrienols, tocopherols, beta-carotene, alpha-carotene, squalene, a plant sterol, CoQ10, a multivitamin, or a combination thereof. The krill oil may be in an amount of about 10 mg to about 2000 mg. The red palm oil may be in an amount of about 10 mg to about 2000 mg. The oleic acid may be in an amount of about 10 mg to about 1000 mg. The linoleic acid may be in an amount of about 1 mg to about 1000 mg. The tocotrienols may be in an amount of about 1 mg to about 1000 mg. The tocopherols may be in an amount of about 1 mg to about 1000 mg. The beta-carotene may be in an amount of about 1 mg to about 1000 mg. The alpha-carotene may be in an amount of about 1 mg to about 1000 mg. The squalene may be in an amount of about 0.1 mg to about 1000 mg. The plant sterol may be in an amount of about 1 mg to about 1000 mg. The CoQ10 may be in an amount of about 0.01 mg to about 1000 mg. The multivitamin may be in an amount of about 1 mg to about 5000 mg.

In some embodiments, the first compartment may comprise krill oil, an omega-3 oil such as, for example, docosahexaenoic acid (DHA), or a combination thereof, and the second compartment may comprise vitamin C, zinc, dicalcium phosphate, vitamin D, vitamin K, magnesium, calcium, or a combination thereof. The krill oil may be in an amount of about 10 mg to about 2000 mg. The DHA may be in an amount of about 10 mg to about 2000 mg. The vitamin C may be in an amount of about 1 mg to about 1000 mg. The zinc may be in an amount of about 1 mg to about 1000 mg. The dicalcium phosphate may be in an amount of about 1 mg to about 1000 mg. The vitamin D may be in an amount of about 10 IU to about 3000 IU. The vitamin K may be in an amount of about 10 mcg to about 1000 mcg. The magnesium may be in an amount of about 0.1 mg to about 1000 mg. The calcium may be in an amount of about 1 mg to about 1000 mg.

In some embodiments, the first compartment may comprise krill oil, and the second compartment may comprise a multivitamin, CoQ10, vitamin A, vitamin D, vitamin D3, vitamin E, biotin, folic acid, niacin, panthothenic acid, vitamin B1, vitamin B2, vitamin B6, vitamin B12, vitamin C, vitamin K, calcium, chromium, copper, iodine, magnesium, magnesium stearate, manganese, molybdenum, phosphorus, selenium, zinc, or a combination thereof. The krill oil may be in an amount of about 10 mg to about 2000 mg. The multivitamin may be in an amount of about 1 mg to about 5000 mg. The CoQ10 may be in an amount of about 0.01 mg to about 1000 mg. The vitamin A may be in an amount of about 10 IU to about 4000 IU. The vitamin D or vitamin D3 may be in an amount of about 10 IU to about 3000 IU. The vitamin E may be in amount of about 10 IU to about 3000 IU. The biotin may be in an amount of about 10 mcg to about 1000 mcg. The folic acid may be in an amount of about 0.1 mcg to about 1000 mcg. The niacin may be in an amount of about 1 mg to about 1000 mg. The panthothenic acid may be in an amount of about 1 mg to about 1000 mg. The vitamin B1 may be in an amount of about 1 mg to about 1000 mg. The vitamin B2 may be in an amount of about 1 mg to about 1000 mg. The vitamin B2 may be in an amount of about 1 mg to about 1000 mg. The vitamin B6 may be in an amount of about 1 mg to about 1000 mg. The vitamin B12 may be in an amount of about 10 mcg to about 1000 mcg. The vitamin C may be in an amount of about 1 mg to about 1000 mg. The vitamin K may be in an amount of about 10 mcg to about 1000 mcg. The calcium may be in an amount of about 1 mg to about 1000 mg. The chromium may be in an amount of about 1 mcg to about 1000 mcg. The copper may be in an amount of about 0.1 mg to about 100 mg. The iodine may be in an amount of about 0.01 mg to about 100 mg. The magnesium may be in an amount of about 0.1 mg to about 1000 mg. The magnesium stearate may be in an amount of about 0.1 mg to about 1000 mg. The manganese may be in an amount of about 0.1 mg to about 100 mg. The molybdenum may be in an amount of about 1 mcg to about 1000 mcg. The phosphorous may be in an amount of about 1 mg to about 100 mg. The selenium may be in an amount of about 1 mcg to about 200 mcg. The zinc may be in an amount of about 1 mg to about 1000 mg.

In some embodiments, the first compartment may comprise red palm oil, and the second compartment may comprise ginseng, CoQ10, vitamin B12, caffeine, caffeine beadlets, or a combination thereof. The red palm oil may be in an amount of about 10 mg to about 2000 mg. The ginseng may be in an amount of about 10 mg to about 1000 mg. The CoQ10 may be in an amount of about 0.01 mg to about 1000 mg. The vitamin B12 may be in an amount of about 10 mcg to about 1000 mcg. The caffeine or caffeine beadlets may be in an amount of about 1 mg to about 1000 mg.

In some embodiments, the first compartment may comprise krill oil, and the second compartment may comprise vitamin D, vitamin D3, calcium, or a combination thereof. The krill oil may be in an amount of about 10 mg to about 2000 mg. The vitamin D or vitamin D3 may be in an amount of about 10 IU to about 3000 IU. The calcium may be in an amount of about 1 mg to about 1000 mg.

In some embodiments, the first compartment may comprise an omega-3 oil, and the second compartment may comprise a probiotic. The omega-3 oil may be in an amount of about 10 mg to about 2000 mg. The probiotic may be in an amount of about 1 million to about 100 million CFUs.

In some embodiments, the first compartment may comprise krill oil, and the second compartment may comprise vitamin K2, glucosamine, collagen, UC2 collagen, or a combination thereof. The krill oil may be in an amount of about 10 mg to about 2000 mg. The vitamin K2 may be in an amount of about 0.01 mg to about 100 mg. The glucosamine may be in an amount of about 10 mg to about 1000 mg. The collagen or UC2 collagen may be in amount of about 1 mg to about 1000 mg.

In some embodiments, the first compartment may comprise an omega-3 oil such as, for example, alpha-linolenic acid (ALA), and the second compartment may comprise caffeine, caffeine beadlets, or a combination thereof. The ALA may be in an amount of about 10 mg to about 2000 mg. The caffeine or caffeine beadlets may be in an amount of about 1 mg to about 1000 mg.

In some embodiments, the first compartment may comprise ginger oil and the second compartment may comprise curcumin. The ginger oil may be in an amount of about 10 mg to about 2000 mg, and the circumin may be in an amount of about 10 mg to about 1000 mg.

In some embodiments, the first compartment may comprise an omega-3 oil, and the second compartment may comprise vitamin D, vitamin D3, vitamin E, folic acid, vitamin B2, vitamin B6, vitamin B12, vitamin C, iron, dicalcium phosphate, or a combination thereof. The omega-3 oil may be in an amount of about 10 mg to about 2000 mg. The vitamin D or vitamin D3 may be in an amount of about 10 IU to about 3000 IU. The vitamin E may be in an amount of about 1 IU to about 3000 IU. The folic acid may be in an amount of about 0.1 mcg to about 1000 mcg. The vitamin B2 may be in an amount of about 1 mg to about 1000 mg. The vitamin B6 may be in an amount of about 1 mg to about 1000 mg. The vitamin B12 may be in an amount of about 1 mcg to about 1000 mcg. The vitamin C may be in an amount of about 1 mg to about 1000 mg. The iron may be in an amount of about 1 mg to about 1000 mg. The dicalcium phosphate may be in an amount of about 1 mg to about 1000 mg.

In some embodiments, the first compartment may comprise krill oil and the second compartment may comprise vitamin D, vitamin D3, vitamin K2, vitamin E, vitamin E tocotrienols, or a combination thereof. The krill oil may be in an amount of about 10 mg to about 2000 mg. The vitamin D or vitamin D3 may be in an amount of about 10 IU to about 3000 IU. The vitamin K2 may be in an amount of about 0.01 mg to about 100 mg. The vitamin E or vitamin E tocotrienols may be in an amount of about 10 mg to about 1000 mg.

In some embodiments, the first compartment may comprise lavender oil, and the second compartment may comprise melatonin, passion flower, lemon, lemon extract, or a combination thereof. The lavender oil may be in an amount of about 10 mg to about 2000 mg. The melatonin may be in an amount of about 1 mg to about 1000 mg. The passion flower may be in an amount of about 10 mg to about 1000 mg. The lemon or lemon extract may be in an amount of about 10 mg to about 1000 mg.

In some embodiments, the first compartment may comprise conjugated linoleic acid (CLA), and the second compartment may comprise piper betle leaf, dolichos bilforus seed extract, or a combination thereof, such as LOWAT. The CLA may be in an amount of about 10 mg to about 2000 mg. The piper betle leaf, dolichos bilforus seed extract, or combination thereof, such as LOWAT, may be in an amount of about 10 mg to about 1000 mg.

In some embodiments, the first compartment may comprise krill oil, and the second compartment may comprise aspirin. The krill oil may be in an amount of about 10 mg to about 2000 mg, and the aspirin may be in an amount of about 10 mg to about 500 mg.

In some embodiments, the first compartment comprising one or more ingredients has a volume of about 50 mm$^3$ to about 1000 mm$^3$, and the second compartment comprising one or more ingredients has a volume of about 50 mm$^3$ to about 1000 mm$^3$. In some embodiments, the volume of the first compartment may be, for example, about 50 mm$^3$, about 75 mm$^3$, about 100 mm$^3$, about 150 mm$^3$, about 200 mm$^3$, about 250 mm$^3$, about 300 mm$^3$, about 350 mm$^3$, about 400 mm$^3$, about 450 mm$^3$, about 500 mm$^3$, about 550 mm$^3$, about 600 mm$^3$, about 650 mm$^3$, about 700 mm$^3$, about 750 mm$^3$, about 800 mm$^3$, about 850 mm$^3$, about 900 mm$^3$, about 950 mm$^3$, about 1000 mm$^3$, or any value between any of these ranges, including any points. In some embodiments, the volume of the second compartment may be, for example, about 50 mm$^3$, about 75 mm$^3$, about 100 mm$^3$, about 150 mm$^3$, about 200 mm$^3$, about 250 mm$^3$, about 300 mm$^3$, about 350 mm$^3$, about 400 mm$^3$, about 450 mm$^3$, about 500 mm$^3$, about 550 mm$^3$, about 600 mm$^3$, about 650 mm$^3$, about 700 mm$^3$, about 750 mm$^3$, about 800 mm$^3$, about 850 mm$^3$, about 900 mm$^3$, about 950 mm$^3$, about 1000 mm$^3$, or any value between any of these ranges, including any points.

One skilled in the art would understand that these examples are not meant to be limiting but are illustrative of the types of ingredients that can be included in the compartments. In the examples above, the ingredient(s) in the first compartment may be in the second compartment, instead, and vice versa.

Table 1 below lists some possible combinations of ingredients which may be found in some embodiments. It is to be understood that any of the ingredients within Table 1 may be found in any combination, and may be found in either compartment of the capsule described herein. It is to be further understood that the embodiments described in Table 1 are not meant to be limiting, but are merely illustrative.

TABLE 1

| First compartment | Second compartment |
| --- | --- |
| About 10 mg to about 500 mg of aspirin | About 10 mg to about 2000 mg of an oil |
| About 10 mg to about 500 mg of aspirin | About 10 mg to about 2000 mg of an omega-3 oil |
| About 10 mg to about 2000 mg of an omega-3 oil; and/or About 10 mg to about 2000 mg of red palm oil | About 10 mg to about 1000 mg of CoQ10 |
| About 10 mg to about 2000 mg of an omega-3 oil | About 1 mg to about 100 mg of a statin; and/or About 10 mg to about 1000 mg of CoQ10 |
| About 10 mg to about 2000 mg of an omega-3 oil | About 10 mcg to about 1000 mcg of vitamin K2 |
| About 10 mg to about 500 mg of alpha linolenic acid | About 10 mcg to about 1000 mcg of chromium; and/or About 10 mg to about 1000 mg of CoQ10 |
| About 10 mg to about 1000 mg of saw palmetto oil | About 5 mcg to about 500 mcg of liothyronine sodium |
| About 10 mg to about 2000 mg of red palm oil | About 10 IU to about 3000 IU of vitamin D; and/or About 10 mcg to about 1000 mcg of vitamin K2; and/or About 1 mg to about 5000 mg of a multivitamin |
| About 10 mg to about 2000 mg krill oil | About 10 mg to about 1000 mg of CoQ10; and/or About 1 mg to about 5000 mg of a multivitamin |
| About 5 mcg to about 500 mcg of triiodothyronine | About 10 mg to about 1000 mg of vitamin B6; and/or About 10 mcg to about 1000 mcg of vitamin B12 |
| About 10 mg to about 2000 mg of krill oil | About 10 mcg to about 1000 mcg of vitamin K2 |
| About 10 mg to about 1000 mg of saw palmetto oil | About 5 mcg to about 500 mcg of triiodothyronine |
| About 10 mg to about 2000 mg of red palm oil | About 1 mg to about 30 mg of lutein; and/or About 1 mg to about 30 mg of lycopene; and/or About 0.01 mg to about 10 mg of biotin; and/or |

TABLE 1-continued

| First compartment | Second compartment |
|---|---|
| | About 1 mcg to about 200 mcg of selenium (methionine); and/or |
| | About 1 mg to about 45 mg of zinc (glyconate) |
| About 10 mg to about 2000 mg of an omega-3 oil | About 1 mg to about 500 mg of frankincense; and/or |
| | About 10 mg to about 1000 mg of gymnema or gymnema extract; and/or |
| | About 10 mg to about 1000 mg of cinnamon; and/or |
| | About 10 mg to about 1000 mg of chromium (picolinate); and/or |
| | About 10 mg to about 1000 mg of vitamin B6; and/or |
| | About 10 mcg to about 1000 mcg of vitamin B12 |
| About 10 mg to about 2000 mg of an omega-3 oil | About 10 mg to about 1000 mg of resvida; and/or |
| | About 1 mg to about 1000 mg of lipoic acid; and/or |
| | About 10 mg to about 1000 mg of CoQ10; and/or |
| | About 0.1 mcg to about 1000 mcg of folic acid; and/or |
| | About 10 mg to about 1000 mg of vitamin B6; and/or |
| | About 10 mcg to about 1000 mcg of vitamin B12 |
| About 10 mg to about 2000 mg of krill oil; and/or | About 10 mg to about 1000 mg of oleic acid; and/or |
| About 10 mg to about 2000 mg of red palm oil | About 1 mg to about 1000 mg of linoleic acid; and/or |
| | About 1 mg to about 1000 mg of tocotrienols; and/or |
| | About 1 mg to about 1000 mg of tocopherols; and/or |
| | About 1 mg to about 1000 mg beta-carotene; and/or |
| | About 1 mg to about 1000 mg alpha-carotene; and/or |
| | About 0.1 mg to about 1000 mg of squalene; and/or |
| | About 1 mg to about 1000 mg of a plant sterol; and/or |
| | About 0.01 mg to about 1000 mg of CoQ10; and/or |
| | About 1 mg to about 5000 mg of a multivitamin |
| About 10 mg to about 2000 mg of krill oil; and/or | About 1 mg to about 1000 mg of vitamin C; and/or |
| About 10 mg to about 2000 mg of an omega-3 oil, such as, for example, docosahexaenoic acid (DHA) | About 1 mg to about 1000 mg of zinc; and/or |
| | About 1 mg to about 1000 mg of dicalcium phosphate; and/or |
| | About 10 IU to about 3000 IU of vitamin D; and/or |
| | About 10 mcg to about 1000 mcg of vitamin K; and/or |
| | About 0.1 mg to about 1000 mg of magnesium; and/or |
| | About 1 mg to about 1000 mg of calcium |
| About 10 mg to about 2000 mg of krill oil | About 1 mg to about 5000 mg of a multivitamin; and/or |
| | About 0.01 mg to about 1000 mg of CoQ10; and/or |
| | About 10 IU to about 4000 IU of vitamin A; and/or |
| | About 10 IU to about 3000 IU of vitamin D or vitamin D3; and/or |
| | About 10 IU to about 3000 IU of vitamin E; and/or |
| | About 10 mcg to about 1000 mcg of biotin; and/or |
| | About 0.1 mcg to about 1000 mcg of folic acid; and/or |
| | About 1 mg to about 1000 mg of niacin; and/or |

TABLE 1-continued

| First compartment | Second compartment |
|---|---|
| | About 1 mg to about 1000 mg of panthothenic acid; and/or |
| | About 1 mg to about 1000 mg of vitamin B1; and/or |
| | About 1 mg to about 1000 mg of vitamin B2; and/or |
| | About 1 mg to about 1000 mg of vitamin B6; and/or |
| | About 10 mcg to about 1000 mcg of vitamin B12; and/or |
| | About 1 mg to about 1000 mg of vitamin C; and/or |
| | About 10 mcg to about 1000 mcg of vitamin K; and/or |
| | About 1 mg to about 1000 mg of calcium; and/or |
| | About 1 mcg to about 1000 mcg of chromium; and/or |
| | About 0.1 mg to about 100 mg of copper; and/or |
| | About 0.01 mg to about 100 mg of iodine; and/or |
| | About 0.1 mg to about 1000 mg of magnesium; and/or |
| | About 0.1 mg to about 1000 mg of magnesium stearate; and/or |
| | About 0.1 mg to about 100 mg of manganese; and/or |
| | About 1 mcg to about 1000 mcg of molybdenum; and/or |
| | About 1 mg to about 100 mg of phosphorous; and/or |
| | About 1 mcg to about 200 mcg of selenium; and/or |
| | About 1 mg to about 1000 mg of zinc |
| About 10 mg to about 2000 mg of red palm oil | About 10 mg to about 1000 mg of ginseng; and/or |
| | About 0.01 mg to about 1000 mg of CoQ10; and/or |
| | About 10 mcg to about 1000 mcg of vitamin B12; and/or |
| | About 1 mg to about 1000 mg of caffeine |
| About 10 mg to about 2000 mg of krill oil | About 10 IU to about 3000 IU of vitamin D or vitamin D3; and/or |
| | About 1 mg to about 1000 mg of calcium |
| About 10 mg to about 2000 mg of an omega-3 oil | About 1 million to about 100 billion CFUs of a probiotic |
| About 10 mg to about 2000 mg of krill oil | About 0.01 mg to about 100 mg of vitamin K2; and/or |
| | About 10 mg to about 1000 mg of glucosamine; and/or |
| | About 1 mg to about 1000 mg of UC2 collagen |
| About 10 mg to about 2000 mg of an omega-3 oil, such as, for example, alpha-linolenic acid (ALA) | About 1 mg to about 1000 mg of caffeine or caffeine beadlets |
| About 10 mg to about 2000 mg of ginger oil | About 10 mg to about 1000 mg of curcumin |
| About 10 mg to about 2000 mg of an omega-3 oil | About 10 IU to about 3000 IU of vitamin D or vitamin D3; and/or |
| | About 1 IU to about 3000 IU of vitamin E; and/or |
| | About 0.1 mcg to about 1000 mcg of folic acid; and/or |
| | About 1 mg to about 1000 mg of vitamin B2; and/or |
| | About 1 mg to about 1000 mg of vitamin B6; and/or |
| | About 1 mcg to about 1000 mcg of vitamin B12; and/or |
| | About 1 mg to about 1000 mg of vitamin C; and/or |
| | About 1 mg to about 1000 mg of iron; and/or |
| | About 1 mg to about 1000 mg of dicalcium phosphate |

TABLE 1-continued

| First compartment | Second compartment |
|---|---|
| About 10 mg to about 2000 mg of krill oil | About 10 IU to about 3000 IU of vitamin D or vitamin D3; and/or About 0.01 mg to about 100 mg of vitamin K2; and/or About 10 mg to about 1000 mg of vitamin E tocotrienols |
| About 10 mg to about 2000 mg of lavender oil | About 1 mg to about 1000 mg of melatonin; and/or About 10 mg to about 1000 mg of passion flower; and/or About 10 mg to about 1000 mg of lemon or lemon extract |
| About 10 mg to about 2000 mg of conjugated linoleic acid (CLA) | About 10 mg to about 1000 mg of a combination of piper betle leaf and/or dolichos biflorus seed extract, such as LOWAT |
| About 10 mg to about 2000 mg of krill oil | About 10 mg to about 500 mg of aspirin |

Table 2 below shows various dimensions of standard and elongated TORPAC capsule sizes, which may be used in some embodiments described herein.

TABLE 2

| CAPSULE SIZE | 000 | 00E | 00 | 00LQ | 0E | 0 | 1 | 2 | 3 | 4 |
|---|---|---|---|---|---|---|---|---|---|---|
| WEIGHT | | | | | | | | | | |
| Average Weight (mg) | 158 | 130 | 123 | 132 | 107 | 99 | 76 | 61 | 48 | 38 |
| tolerance | ±10 | ±10 | ±7 | ±4 | ±7 | ±6 | ±5 | ±4 | ±3 | ±3 |
| CAPACITY | | | | | | | | | | |
| Volume Capacity (ml) | 1.37 | 1.02 | 0.95 | 0.95 | 0.77 | 0.68 | 0.48 | 0.36 | 0.27 | 0.20 |
| density of dosing powder | | | | Weight Capacity (mg) | | | | | | |
| 0.6 g/ml | 822 | 612 | 570 | 570 | 462 | 408 | 288 | 216 | 162 | 120 |
| 0.8 g/ml | 1096 | 816 | 760 | 760 | 616 | 544 | 384 | 288 | 216 | 160 |
| 1.0 g/ml | 1370 | 1020 | 950 | 950 | 770 | 680 | 480 | 360 | 270 | 200 |
| 1.2 g/ml | 1644 | 1224 | 1140 | 1140 | 924 | 816 | 576 | 432 | 324 | 240 |
| OVERALL CLOSED LENGTH | | | | | | | | | | |
| (mm) | 26 | 25.4 | 23.4 | 23.4 | 23.4 | 21.6 | 19.4 | 17.6 | 15.7 | 14.3 |
| tolerance | ±0.3 | ±0.3 | ±0.3 | ±0.3 | ±0.3 | ±0.3 | ±0.3 | ±0.3 | ±0.3 | ±0.3 |
| (inches) | 1.024 | 1 | 0.921 | 0.921 | 0.921 | 0.85 | 0.764 | 0.693 | 0.618 | 0.563 |
| tolerance | ±0.012 | ±0.012 | ±0.012 | ±0.012 | ±0.012 | ±0.012 | ±0.012 | ±0.012 | ±0.012 | ±0.012 |
| INDIVIDUAL LENGTHS (CAP & BODY) | | | | | | | | | | |
| CAP (mm) | 12.9 | 12.94 | 11.8 | 11.8 | 11.9 | 10.85 | 9.85 | 8.8 | 8 | 7.2 |
| tolerance | ±0.35 | ±0.5 | ±0.35 | ±0.35 | ±0.35 | ±0.35 | ±0.35 | ±0.35 | ±0.35 | ±0.35 |
| BODY (mm) | 21.9 | 22.38 | 20.1 | 20.1 | 20 | 18.45 | 16.4 | 15.15 | 13.45 | 12.1 |
| tolerance | ±0.35 | ±0.35 | ±0.35 | ±0.35 | ±0.35 | ±0.35 | ±0.35 | ±0.35 | ±0.35 | ±0.35 |
| CAP (inches) | 0.508 | 0.509 | 0.464 | 0.464 | 0.468 | 0.427 | 0.388 | 0.346 | 0.315 | 0.283 |
| tolerance | ±0.014 | ±0.014 | ±0.014 | ±0.014 | ±0.014 | ±0.014 | ±0.014 | ±0.014 | ±0.014 | ±0.014 |
| BODY (inches) | 0.862 | 0.881 | 0.791 | 0.791 | 0.787 | 0.726 | 0.646 | 0.596 | 0.529 | 0.476 |
| tolerance | ±0.014 | ±0.014 | ±0.014 | ±0.014 | ±0.014 | ±0.014 | ±0.014 | ±0.014 | ±0.014 | ±0.014 |
| EXTERNAL DIAMETER | | | | | | | | | | |
| CAP (mm) | 9.94 | 8.58 | 8.56 | 8.56 | 7.66 | 7.65 | 6.96 | 6.39 | 5.85 | 5.33 |
| BODY (mm) | 9.55 | 8.25 | 8.23 | 8.23 | 7.35 | 7.35 | 6.63 | 6.12 | 5.60 | 5.08 |
| CAP (inches) | 0.391 | 0.338 | 0.337 | 0.337 | 0.302 | 0.301 | 0.274 | 0.252 | 0.23 | 0.21 |
| BODY (inches) | 0.376 | 0.325 | 0.324 | 0.324 | 0.289 | 0.289 | 0.261 | 0.241 | 0.22 | 0.2 |

Recommended Storage Conditions: 59°-77° F./15°-25° C. RH 35-65%

Table 3 below shows additional dimensions of standard and elongated TORPAC capsule sizes, which may be used in some embodiments described herein.

TABLE 3

| Size | Typical Fill Weights (mg) Actual Fill Weights may vary and depend on powder characteristics Powder Density | | | Volume | Locked Length | Tolerance Component | External Diam. | Cut Length | Single Wall Thickness | Weight (Avg. of 100) |
|---|---|---|---|---|---|---|---|---|---|---|
| | 0.45 Light | 0.70 Typical | 1.00 Heavy | Theoretical (ml) | +/−0.76 (mm) | | (mm) | +/−0.51 (mm) | +/−0.03 (mm) | +/−10% (mg) |
| 000 | 615 | 960 | 1370 | 1.37 | 26.14 | Cap | 9.91 | 12.95 | 0.112 | 163 |
| | | | | | | Body | 9.55 | 22.20 | 0.110 | |
| 00 | 430 | 665 | 950 | 0.95 | 23.30 | Cap | 8.53 | 11.74 | 0.109 | 118 |
| | | | | | | Body | 8.18 | 20.22 | 0.107 | |
| 0 | 305 | 475 | 680 | 0.68 | 21.70 | Cap | 7.65 | 10.72 | 0.107 | 96 |
| | | | | | | Body | 7.34 | 18.44 | 0.104 | |
| 1 | 225 | 350 | 500 | 0.50 | 19.40 | Cap | 6.91 | 9.78 | 0.104 | 76 |
| | | | | | | Body | 6.63 | 16.61 | 0.102 | |
| 2 | 165 | 260 | 370 | 0.37 | 18.00 | Cap | 6.35 | 8.94 | 0.102 | 61 |
| | | | | | | Body | 6.07 | 15.27 | 0.099 | |
| 3 | 135 | 210 | 300 | 0.30 | 15.90 | Cap | 5.82 | 8.08 | 0.092 | 48 |
| | | | | | | Body | 5.56 | 13.59 | 0.890 | |
| 4 | 95 | 145 | 210 | 0.21 | 14.30 | Cap | 5.31 | 7.21 | 0.096 | 38 |
| | | | | | | Body | 5.05 | 12.19 | 0.091 | |
| 5 | 60 | 90 | 130 | 0.13 | 11.10 | Cap | 4.91 | 6.20 | 0.089 | 28 |
| | | | | | | Body | 4.68 | 9.32 | 0.086 | |

Although the present invention has been described in considerable detail with reference to certain preferred embodiments thereof, other versions are possible. Therefore, the spirit and scope of the appended claims should not be limited to the description and the preferred versions contained within this specification. Modifications and improvements to the disclosed embodiments will be apparent to those skilled in the art in light of this disclosure, and are intended to fall within the scope of the pending claims.

The invention claimed is:

1. A multi-compartment capsule comprising:
a body;
a diaphragm, having two sidewalls and a bottom, extending into the body and defining a first compartment between an outer surface of the diaphragm and an inner surface of the body; and
a cap mounted to an outer surface of the body and opposed to the diaphragm, and defining a second compartment between an inner surface of the diaphragm and the cap;
wherein the two sidewalls of the diaphragm extend along and contact the inner surface of the body and are aligned with an open end of the body, forming a seal between the diaphragm and the body;
wherein the first compartment is configured to have a volume of about 423 mm³ to about 743 mm³ and contains a first ingredient;
wherein the second compartment is configured to have a volume of about 176 mm³ to about 497 mm³ and contains a second ingredient;
wherein the multi-compartment capsule has a total volume of about 910 mm³ to about 950 mm³, containing the first compartment and the second compartment therein; and
wherein the multi-compartment capsule is configured to co-administer the first ingredient and the second ingredient during digestion.

2. The capsule of claim 1, wherein the volume ratio of the first compartment to the second compartment is about 0.84 to about 4.2.

3. The capsule of claim 1, wherein the length of the second compartment is about 5 mm to about 11.75 mm.

4. The capsule of claim 1, wherein the length of the second compartment is less than 7 mm.

5. The capsule of claim 1, wherein the length of the second compartment is greater than 10 mm.

6. The capsule of claim 1, wherein the length of the first compartment is about 8 mm to about 25 mm.

7. The capsule of claim 1, wherein the capsule is about 23.5 mm in length.

8. The capsule of claim 1, wherein the length of contact between a sidewall of the diaphragm and a sidewall of the body is about 0.91 mm to about 8.5 mm.

9. The capsule of claim 1, wherein the bottom of the diaphragm has a shape selected from the group consisting of curved and flattened.

10. The capsule of claim 1, wherein the first ingredient and the second ingredient are each volume-critical.

11. The capsule of claim 1, wherein the first compartment has a sufficient volume to administer a therapeutically effective dose of the first ingredient, and wherein the second compartment has a sufficient volume to administer a therapeutically effective dose of the second ingredient.

12. The capsule of claim 1, wherein the second ingredient is aspirin in an amount of about 10 mg to about 800 mg and the first ingredient is an oil in an amount of about 10 mg to about 700 mg.

13. The capsule of claim 1, wherein the first ingredient is an oil selected from the group consisting of omega-3 oil, red palm oil, fish oil, hill oil, walnut oil, saw palmetto oil, castor oil, garlic oil, flaxseed oil, canola oil, soybean oil, cannabis oil, argan oil, coconut oil, peppermint oil, evening primrose oil, oregano oil, emu oil, cod liver oil, algae oil, grape seed oil, rose oil, clove oil, vitamin E oil, blueberry seed oil, raspberry seed oil, pumpkin seed oil, hemp oil, alpha linolenic acid, conjugated linoleic acid, docosahexaenoic acid, ginger oil, lavender oil, and combinations thereof.

14. The capsule of claim 1, wherein the second ingredient is selected from the group consisting of alpha-carotene, beta-carotene, biotin, cadmium, caffeine, calcium, cinnamon, copper, curcumin, dexmethylphenidate, dicalcium phosphate, docosahexaenoic acid, folic acid, frankincense, glucosamine, gymnema, gymnema extract, iodine, iron, linoleic acid, lipoic acid, piper betle leaf, dolichos bilforus seed extract, lutein, lycopene, magnesium, magnesium stearate, manganese, melatonin, molybdenum, niacin, oleic acid, palmitic acid, panthothenic acid, passion flower, phosphorus, a plant sterol, resvida, selenium, squalene, ginseng, tocopherols, vitamin A, vitamin B1, vitamin B2, vitamin B6, vitamin C, vitamin K, zinc, and combinations thereof.

15. The capsule of claim 1, wherein the first ingredient is a tocotrienol and the second ingredient is selected from vitamin B6, vitamin B 12, or a combination thereof.

16. The capsule of claim 1, wherein the second ingredient is selected from an oil, a powder, a liquid, a microbead, a beadlet, a granule, a semi-solid, a gel, or a combination thereof.

17. A multi-compartment capsule comprising:
a body;
a diaphragm, having two sidewalls and a bottom, extending into the body and defining a first compartment between an outer surface of the diaphragm and an inner surface of the body; and
a cap mounted to an outer surface of the body and opposed to the diaphragm, and defining a second compartment between an inner surface of the diaphragm and the cap;
wherein the two sidewalls of the diaphragm extend along and contact the inner surface of the body and are aligned with an open end of the body, forming a seal between the diaphragm and the body;
wherein the first compartment is configured to have a volume between 45% and 80% of a total volume of the multi-compartment capsule;
wherein the first compartment contains a first ingredient and the second compartment contains a second ingredient; and
wherein the total volume of the multi-compartment capsule is from about 910 mm$^3$ to about 950 mm$^3$, containing the first compartment and the second compartment therein.

* * * * *